United States Patent [19]
Vandemoortele et al.

[11] Patent Number: 6,045,545
[45] Date of Patent: *Apr. 4, 2000

[54] DISPOSABLE ABSORBENT ARTICLE

[75] Inventors: Philippe Vandemoortele, Lille; Jean-Pierre Koczab, Bondues; Albert Villez, Linselles, all of France

[73] Assignee: Peaudouce, Linselles, France

[*] Notice: This patent issued on a continued prosecution application filed under 37 CFR 1.53(d), and is subject to the twenty year patent term provisions of 35 U.S.C. 154(a)(2).

[21] Appl. No.: 08/760,226

[22] Filed: Dec. 4, 1996

Related U.S. Application Data

[63] Continuation of application No. 08/244,101, filed as application No. PCT/FR92/01076, Nov. 20, 1992, abandoned.

[30] Foreign Application Priority Data

Nov. 22, 1991 [FR] France ................................. 91 14399

[51] Int. Cl.⁷ .................................................... A61B 13/15
[52] U.S. Cl. .................... 604/385.2; 604/382; 604/385.1
[58] Field of Search ............................. 604/385.1, 385.2, 604/386, 397, 398, 382

[56] References Cited

U.S. PATENT DOCUMENTS

| | | | |
|---|---|---|---|
| 3,999,547 | 12/1976 | Hernandez | 604/370 |
| 3,999,548 | 12/1976 | Hernandez | 604/370 |
| 4,808,178 | 2/1989 | Aziz et al. | |
| 5,569,227 | 10/1996 | Vandemoortele | 604/385.2 |
| 5,582,606 | 12/1996 | Bruemmer et al. | 604/385.2 |
| 5,584,828 | 12/1996 | Yamamoto et al. | 604/385.2 |

FOREIGN PATENT DOCUMENTS

| | | |
|---|---|---|
| 243 013 A1 | 10/1987 | European Pat. Off. |
| 391 476 A3 | 10/1990 | European Pat. Off. |
| 2126850 | 5/1990 | Japan |
| 2-152451 | 6/1990 | Japan |
| 2271863 | 11/1990 | Japan |
| 22 80 62 | 12/1990 | New Zealand |

*Primary Examiner*—John G. Weiss
*Assistant Examiner*—K. M. Reichle
*Attorney, Agent, or Firm*—Burns, Doane, Swecker & Mathis, L.L.P.

[57] ABSTRACT

A disposable absorbent article of hygiene includes an absorbent pad disposed between an outer support sheet and an inner cover sheet and has two elasticized side flaps fastened to the cover sheet along the lengthwise edges of the article. Each flap is fastened to the cover sheet over the length of the article by a proximal portion of the flap positioned on an inner side of the absorbent pad, and is folded along the lengthwise direction. The flap is also fastened to the cover sheet in the folded state at end regions of the article so that a distal edge of the flap overlaps the proximal edge over the length of the article, and remains unattached in a region between the end regions to form a pouch.

7 Claims, 5 Drawing Sheets

DISPOSABLE ABSORBENT ARTICLE

This application is a continuation of application Ser. No. 08/244,101, filed May 19, 1994, now abondoned, which was filed under 35 U.S.C. § 371 as the national stage application of international application PCT/FR92/01076, filed Nov. 20, 1992, which claimed priority to French Application No. 91/14399, filed Nov. 22, 1991.

FIELD OF THE INVENTION

The present invention relates to a disposable absorbent article of hygiene, especially a diaper, of the type comprising a liquid-impervious outer support sheet, a liquid-permeable inner cover sheet, an absorbent pad arranged between the two sheets, lengthwise elastic members attached in the stretched state to the said support sheet, outside the two lengthwise edges of the absorbent pad, two elasticised side flaps attached to the cover sheet along the lengthwise edges of the article of hygiene, and means of fastening for closing the article of hygiene around a user's waist.

BACKGROUND AND SUMMARY

Articles of hygiene of this type are known from Patent Application GB-A-2,161,059 and from other, more recent documents, for example Patent Applications EP-A-219,326, 243,013, 374,640 and 391,476.

An article of hygiene of this type exhibiting a rectangular general shape may incorporate two opposed side cutouts imparting a so-called anatomical or hour-glass shape to the article of hygiene. Such an article of hygiene, whether provided with such side cutouts or not, has, in its length direction, a rear part corresponding to a lengthwise end region, a front part corresponding to the other lengthwise end region and a crotch part corresponding to the intermediate region of the nappy of the diaper. In an article of hygiene of anatomical or hourglass shape, the crotch part has a width which is smaller than the front part and the rear part.

The side flaps with which the articles of hygiene according to the abovementioned prior documents are provided are intended to improve the general leakproofing of the article of hygiene in the crotch part, as well as the action of confining urine and faecal matter. These side flaps forming the side barrier effect are arranged on the inner face of the cover sheet, that is to say the face in contact with the user's skin, and are spaced transversely so as to extend substantially along the lengthwise edges of the article of hygiene. These side flaps can either be formed directly in the material of the cover sheet, as proposed by Patent Application GB-A-2,161,059, or may consist of tapes made of material which is permeable or impervious to liquids and which are fastened to the inner face of the cover sheet. In all cases these flaps are joined by one of their lengthwise edges, called the proximal edge, to the cover sheet, and, at their other lengthwise edge called the distal edge, that is to say their free edge, carry an elastic member consisting, for example, of one or a number of elastic threads or strands which are preferably attached by adhesive bonding in the stretched state to the flap. This elastic member may, for example, be arranged in a sheath or a gusset formed by folding back the lengthwise edge of the tape onto itself, at least over the middle part of the length of this tape, corresponding to the crotch region of the article of hygiene, it being possible for the elastic member to be fastened to the flap either over its whole length or only at its two ends. In both lengthwise end regions of the article of hygiene, the distal edges of the flaps are fastened to the cover sheet, for example by a transverse adhesive bonding line or strip, so that here the flaps are arranged flat on the cover sheet, the distal edges of the two opposed flaps pointing either inwards, that is to say towards each other, or outwards, that is to say away from each other.

The first solution presents problems when the proximal edges of the flaps, in case of an article of hygiene of anatomical or hourglass shape, are arranged above the absorbent pad in the narrower crotch part, insofar as the distal edges of the two opposed flaps are then too close to each other, and this limits the leakproofing and the action of confining urine and faecal matter in the case of articles of hygiene in which the absorbent pad is also narrower in this crotch part.

The solutions proposed by the other abovementioned prior documents generally consist in fastening the flaps so that, in the crotch part of the article of hygiene, their proximal edges are situated outside the side edges of the absorbent pad, that is to say in a region where the cover sheet is fastened to the support sheet. In this case, owing to the thickness of the absorbent pad, these flaps must be relatively large in height to be able to provide a satisfactory barrier effect and must be largely independent in relation to the remaining part of the article of hygiene (absorbent pad, outer support sheet, lengthwise elastic members fastened to the outer support sheet), and this increases the unit cost of the article of hygiene equipped with such side flaps.

It therefore appears that the solutions proposed hitherto are not entirely satisfactory.

The present document relates to an article of hygiene of the type defined above, particularly an article of hygiene of so-called anatomical or hourglass shape, with a narrower absorbent pad in the crotch part, in which the side flaps are designed so as to provide an optimal barrier effect at a reduced cost.

The disposable absorbent article of hygiene in accordance with the invention, especially a diaper, is of substantially rectangular general shape with opposed lengthwise edges and opposed transverse edges and comprises, from the outside inwards, a liquid-impervious support sheet, an absorbent pad arranged and fastened to the inner face of the support sheet, the dimensions of the pad being smaller than those of the support sheet, and a liquid-permeable cover sheet at least partially covering the inner face of the absorbent pad and fastened at least partially to the support sheet on the periphery of the absorbent pad. In addition, this article comprises lengthwise elastic members fastened in the stretched state to the support sheet, outside the lengthwise edges of the absorbent pad. Furthermore, the article comprises two transversely spaced side flaps arranged on the inner face of the cover sheet, substantially along the lengthwise edges of the article of hygiene, each of the said flaps having a proximal edge connected to the cover sheet and a distal edge comprising a stretched lengthwise elastic member. In addition, the article of hygiene comprises fastening means, in the vicinity of one of its transverse edges, in order to close the article of hygiene around a user's waist so that the article of hygiene defines a front part and a rear part corresponding respectively to the two end regions near the said opposed transverse edges of the article of hygiene, and a crotch part corresponding to the intermediate region situated between the two said end regions. According to the invention, each of the said side flaps is fastened to the cover sheet along its proximal edge, over the whole length of the article of hygiene, so that the said proximal edge is above the absorbent pad over the whole length of the article of hygiene, including in the crotch part. This flap is folded back onto itself over its whole length, and is fastened to the cover sheet in the end parts of the article of hygiene, so that its elasticised distal edge is substantially above its proximal edge over the whole length of the flap.

Thus, the proximal edge of each side flap is situated as close as possible to the user's skin as a result of its arrangement above the absorbent pad. In addition, since the elasticised distal edge of each flap is situated substantially above the proximal edge, the distal edges of both flaps are sufficiently far from each other and can follow the user's movements in an optimal manner, thus allowing the flaps always to maintain their barrier effect. Furthermore, the proximal edge of the flaps is at a maximum distance from the lengthwise elastic members fastened to the outer support sheet, and this makes the flap largely independent in relation to the other parts of the diaper, especially the absorbent pad and the lengthwise elastic members fastened to the support sheet.

Within the scope of the invention, each flap can be folded back onto itself outwards or, preferably, inwards. In the latter case each flap by itself forms a pouch in the crotch part when its elasticised distal edge is raised in relation to its proximal edge, that is to say in relation to the cover sheet, thus improving the barrier effect.

BRIEF DESCRIPTION OF THE DRAWINGS

A more detailed description of a number of illustrative and nonlimiting embodiments of an article of hygiene in accordance with the invention will be given below with reference to the attached diagrammatic drawings; in the drawings.

DETAILED DESCRIPTION

Figure 1:
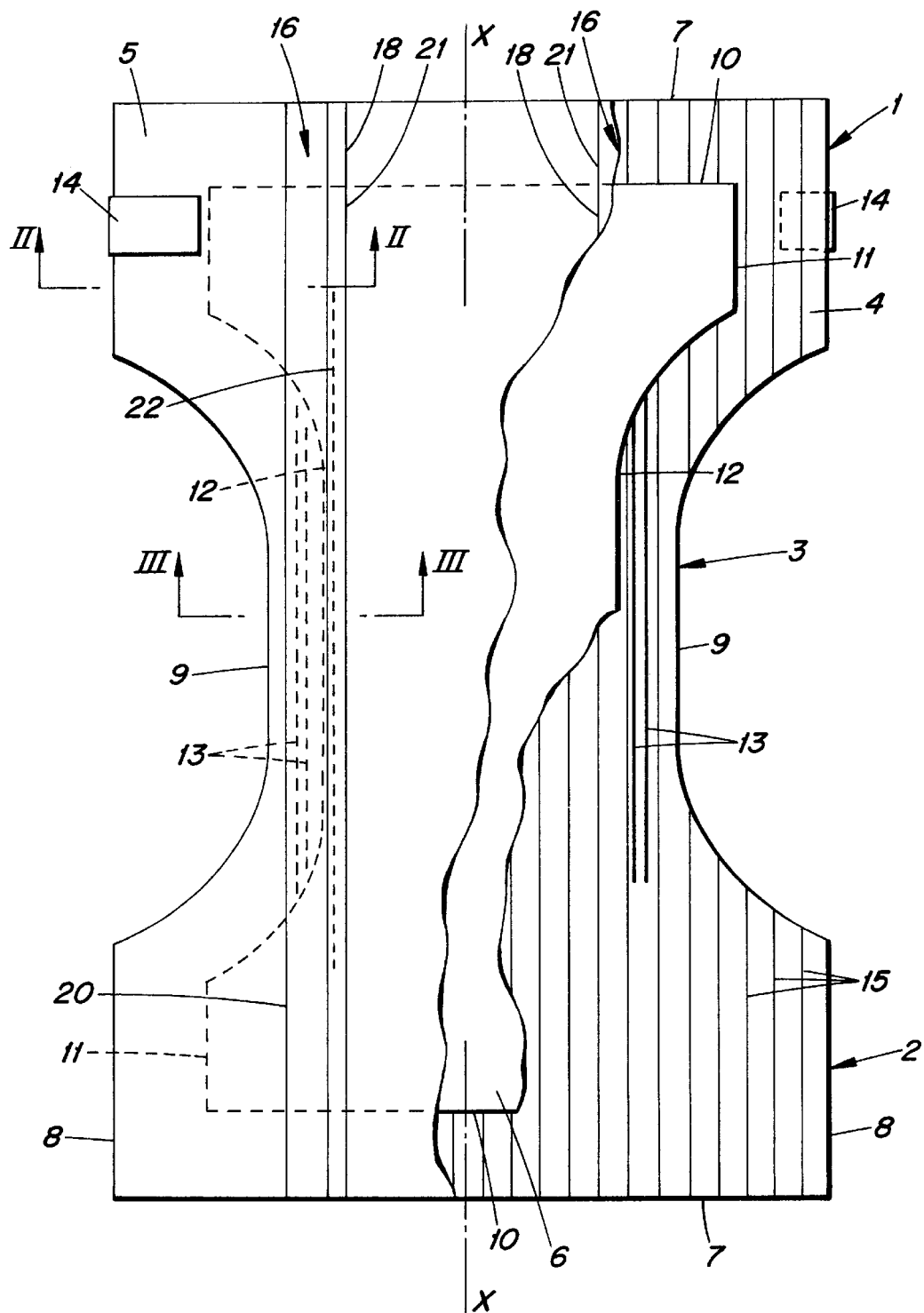
FIG. 1 is a view of the inner face of a diaper in accordance with the invention, laid flat and partially cut-away to illustrate the layers of the article.
Figure 2:
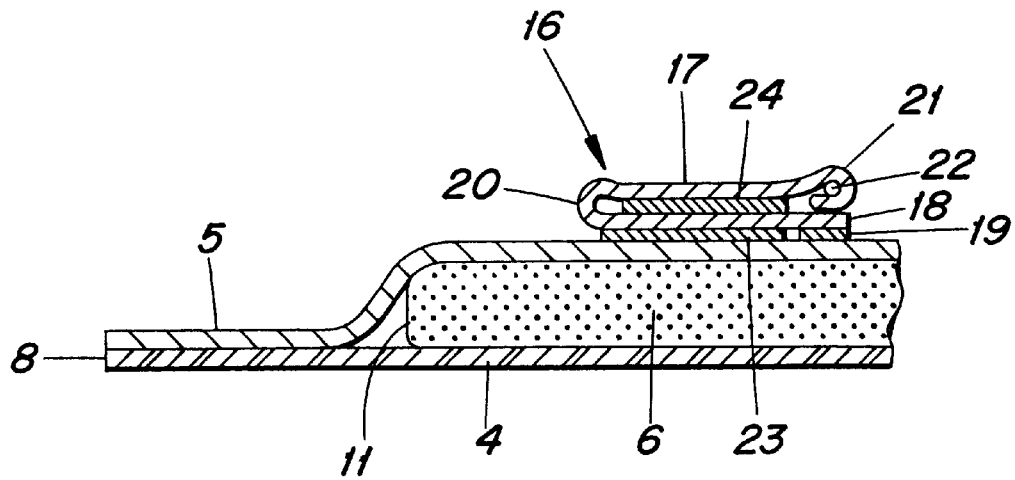
FIG. 2 is a partial section, on a larger scale, along II—II of FIG. 1, in an end part of the diaper.
Figure 3:
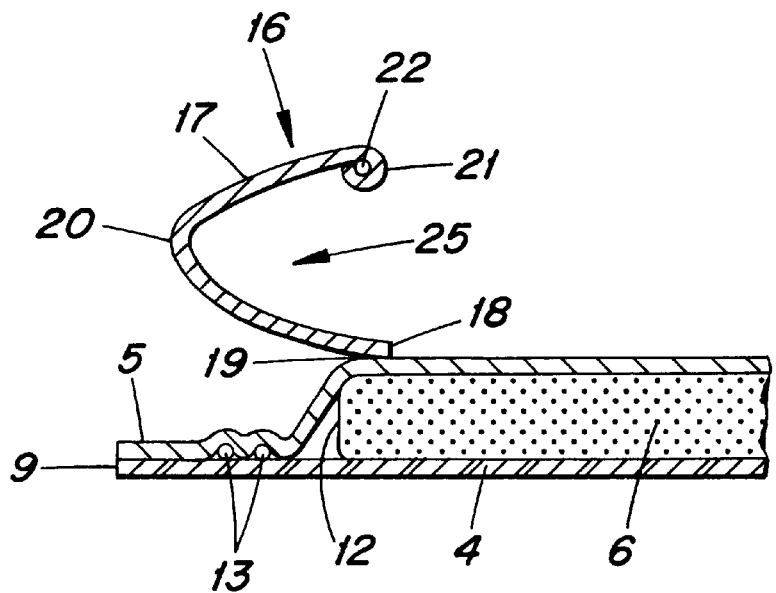
FIG. 3 is a partial section, on a larger scale, along III—III of FIG. 1, in the crotch part of the diaper.

The disposable diaper as illustrated by FIGS. 1 to 3 is a so-called anatomical or hourglass diaper, which has two opposed side cutouts making it possible to define, in the length direction of the diaper, a rear part 1 corresponding to a lengthwise end region, a front part 2 corresponding to the other lengthwise end region and a crotch part 3 corresponding to the intermediate region of the diaper. In the crotch part 3 the diaper is less wide than in the front part 1 and in the rear part 2.

The general structure of the diaper in accordance with FIGS. 1 to 3 corresponds to that of the traditional diaper comprising, from the outside inwards, that is to say from the bottom up in FIGS. 2 and 3, a liquid-impervious outer support sheet 4, a liquid-permeable inner cover sheet 5 and an absorbent pad 6 arranged between the two sheets 4 and 5.

According to FIG. 1, the two sheets 4 and 5 are of the same size and the same shape, namely a rectangular general shape with two opposed rectilinear transverse edges 7 and two opposed lengthwise edges 8, each comprising an indentation 9 substantially in the middle of its length, and this gives both sheets 4 and 5 their hourglass shape, the indentations 9 defining the narrower crotch part 3.

The absorbent wadding or pad 6 arranged between the two sheets 4 and 5 which is also hourglass-shaped is of a smaller size in relation to that of the sheets 4 and 5 and is centered in relation to these sheets 4 and 5 so that its rectilinear transverse edges 10 and its two lengthwise edges 11, each provided with an indentation 12 substantially in the middle of its length, are set back inwards in relation to the corresponding edges 7 and 8 of the two sheets 4 and 5, respectively.

Furthermore, the diaper comprises, in a manner known per se, two lengthwise elastic members 13, each consisting, in the example shown, of two elastic strands spaced apart and fastened in the stretched state to the outer sheet 4, at least in the crotch part 3, between the bottom of the indentations 12 of the absorbent pad 6 and the bottom of the indentations 9 in the sheets 4 and 5.

Two adhesive fastenings 14 are provided in a manner known per se on the rear part 1, with a view to the closing of the diaper around a user's waist, the fastenings 14 then interacting with the front part 2 of the diaper.

The means for fastening the absorbent pad 6 to the outer sheet 4 and for fastening the inner sheet 5 to the outer sheet 4, around the pad 6, are shown in the form of lengthwise lines of adhesive 15. On the other hand, the means for fastening the elastic members 13 to the outer sheet 4 have not been shown, it being possible for these means, which are known per se, to consist, for example, of lines or coatings of adhesive.

The lengthwise middle axis X—X of the diaper is also shown in FIG. 1.

On its inner face, that is to say its face which can be seen in FIG. 1, which is the face turned towards the user, the inner sheet 5 carries two side flaps or folds 16 forming a side barrier, these flaps 16 being transversely spaced and arranged symmetrically on each side of the lengthwise axis X—X.

As can be seen especially in FIGS. 2 and 3, each flap 16 consists of a tape 17 extending over the whole length of the diaper, fastened over its whole length by its proximal edge 18 to the inner sheet 5 above the pad 6, by adhesive bonding, welding or any other appropriate process, along a lengthwise line or strip 19 which, in the crotch part 3, is situated inside the lengthwise edge of the pad 6, which edge is defined here by the bottom of the indentation 12.

Starting from the fastening line 19, the tape 17 extends outwards and is folded symmetrically back onto itself inwards, over its whole length, along the fold line 20, so as to form two substantially equal folds and so that the distal edge 21 of the tape 17 is substantially above the proximal edge 18. The distal edge 21 of the tape 17 is elasticised at least over the middle part of the length of the tape, corresponding to the crotch part 3. In the example shown, the elastic member 22 is fastened by adhesive bonding in a sheath or a gusset formed by folding the proximal edge of the tape back on to itself.

In the two end parts 1 and 2 of the diaper, the tape 17 is fastened in this folded-back position to the inner sheet 5. As FIG. 2 shows, this fastening is performed by adhesive bonding, welding or any other appropriate process along a first transverse line 23 by which the inner fold of the tape 17 is integrally fastened to the inner sheet 5, and along a second transverse strip 24, by which the upper fold of the tape 17 is integrally fastened to the lower fold of the latter.

This fastening of the flap 16 in the folded-back position to the inner sheet 5 of the diaper, in the two end parts 1 and 2 of the, latter, makes sure that the flap 16, under the tension of the elastic member 22, opens in the way which can be seen in FIG. 3 in the crotch part, forming here a pouch 25 disposed transversely outward of the absorbent pad 61 and whose elasticised free edge defined by the distal edge 21 of the tape 17 is positioned above the proximal edge 18 of the flap 16. Consequently, the distal edges 21 of the two opposed flaps 16 are separated from each other by a distance corresponding substantially to the distance separating the proximal edges 18 of the two opposed flaps 16.

Figure 4:
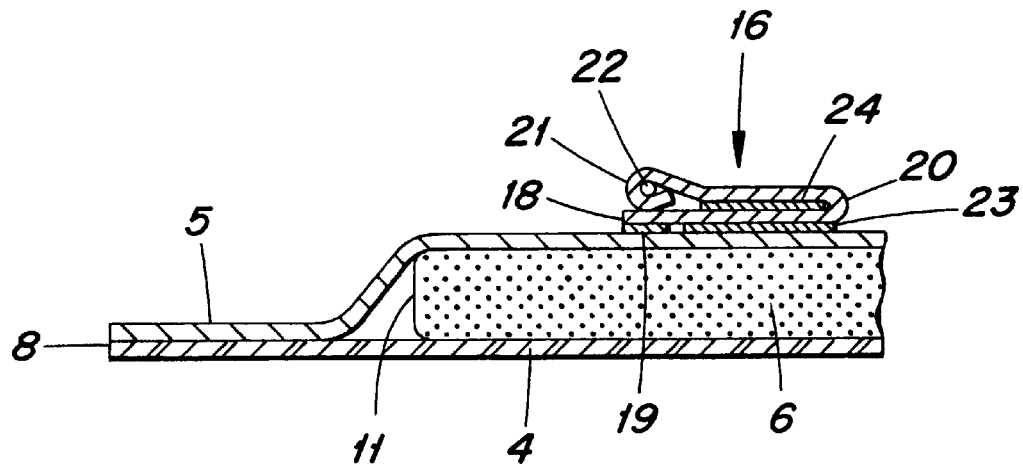
FIGS. 4 and 5 are partial sections, corresponding to FIGS. 2 and 3, of an alternative embodiment of a diaper in accordance with the invention.
Figure 5:
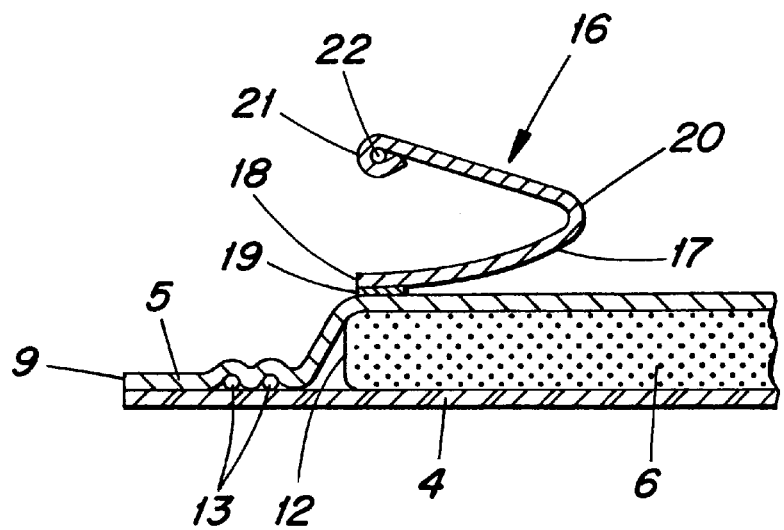

In the embodiment according to FIGS. 4 and 5, the same general structure of the diaper according to FIGS. 1 to 3 is found again, with an outer support sheet 4 and an inner cover sheet 5, both hourglass-shaped, an absorbent pad 6, also hourglass-shaped, lengthwise elastic members 13 situated outside the pad 6 in the crotch part 3 of the diaper, and two side flaps 16, each consisting of a lengthwise tape 17. Here, too, this tape 17 is connected at its proximal edge 18 by a lengthwise strip or line 19 to the lower sheet 5, above the absorbent pad 6, even in the crotch part of the diaper, in which the pad 6 comprises side indentations 12. Similarly, the distal edge 21 of the tape 17 is elasticised by virtue of the presence of a stretched elastic member 22, and the tape 17 is folded back onto itself and fastened to the inner sheet 5, in this folded-back state, in the end parts 1 and 2 of the diaper by two transverse lines or strips 23 and 24.

However, in this embodiment, the tape 17 of each flap 16 is fastened by its proximal edge 18 to the lower sheet 5 so that the tape 17 extends from the said proximal edge towards the interior of the diaper, that is to say in the direction of the opposed flap 16, and is folded back around the fold line 20 outwards, that is to say in the opposite direction to the preceding embodiment. Here, too, the elasticised distal edge 21 of each flap 16 is thus always positioned substantially above the proximal edge 18, even in the crotch part 3 of the diaper in which the distal edge 21 of the flap 16 can be raised from the inner sheet 5 by the action of its elastic member 22.

Figure 6:
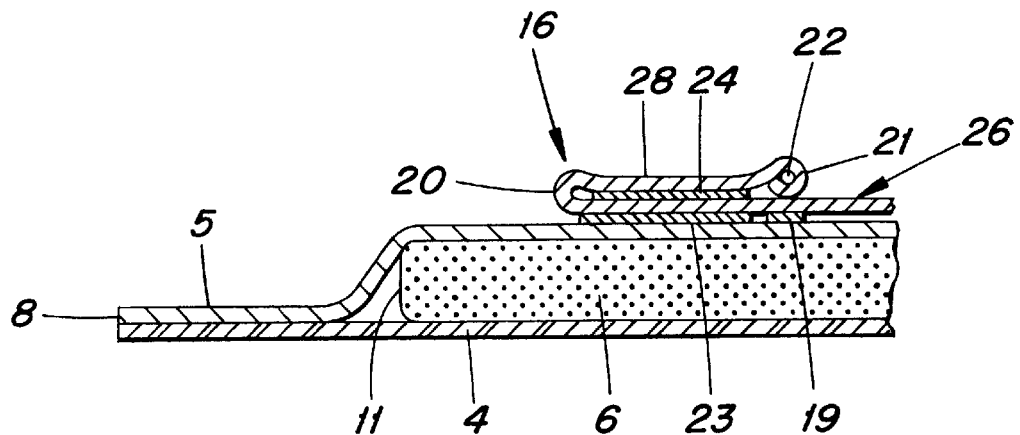
FIGS. 6 and 7 are partial sections, corresponding to FIGS. 2 and 3, of another alternative embodiment of a diaper in accordance with the invention.
Figure 7:
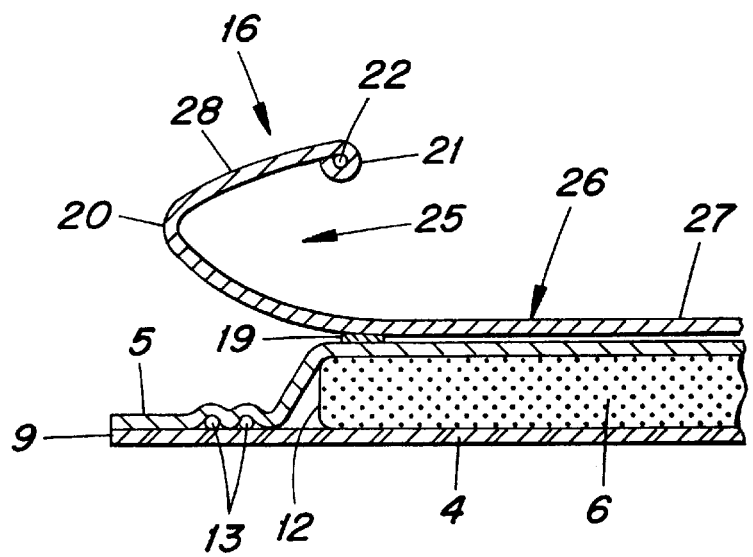

In the alternative embodiment illustrated by FIGS. 6 and 7 the general structure of the diaper according to FIGS. 1 to 3 is to be found again including the two side flaps 16 which extend outwards from their proximal edges defined by the lengthwise fastening lines or strips 19, and are folded back onto themselves inwards. On the other hand, the two flaps 16, instead of each consisting of a separate tape, here form part of a single lengthwise tape 26 the width of which is greater than the width of the absorbent pad 6 in the crotch part, that is to say at the site of the indentations 12.

This tape 26 is fastened along the two lengthwise lines 19 to the inner sheet 5, above the absorbent pad 6, so that the middle part 27 of the tape 26, included between the two lines 19, covers the inner sheet 5 above the absorbent pad 6, and so that the two side parts 28 of the tape 26, which are situated beyond the lines 19, extend outwards. Each side part 28 is folded back onto itself inwards (fold line 20) and is elasticised at its distal edge 21, at least in the crotch part of the diaper, by virtue of the presence of an elastic member 22 fastened in the stretched state to the said edge.

Here, too, in both end parts of the diaper, the two folds of each flap 16 are fastened flat to each other by a transverse line or strip 24 and to the inner sheet 5 by a transverse line or strip 23, as shown in FIG. 6, with the result that the elasticised distal edge 21 of each flap 16 is capable, in the crotch part of the diaper, of being raised from the inner sheet 5 while remaining positioned substantially above the proximal edge defined by the line 19. In this way each of the two flaps 16 opens in the form of a pouch 25 elasticised on its free edge.

Figure 8:
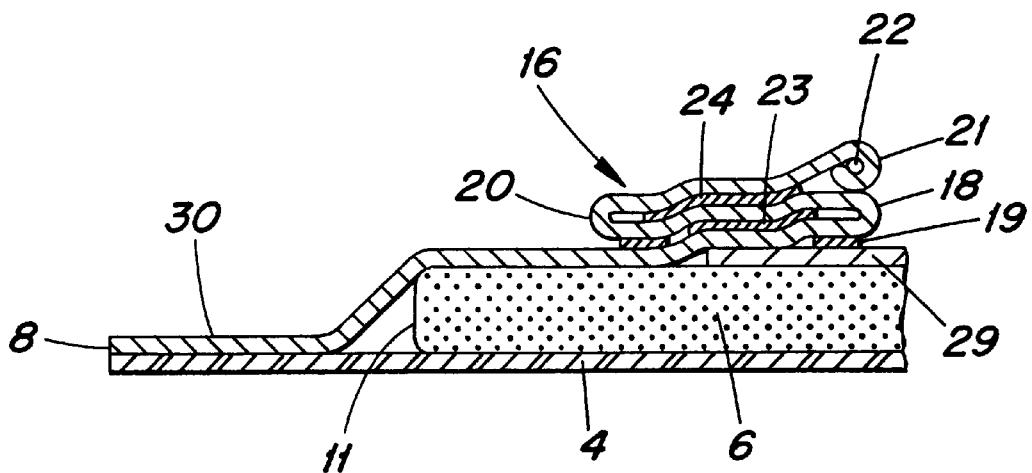
FIGS. 8 and 9 are partial sections, corresponding to FIGS. 2 and 3, of yet another alternative embodiment of a diaper in accordance with the invention.
Figure 9:
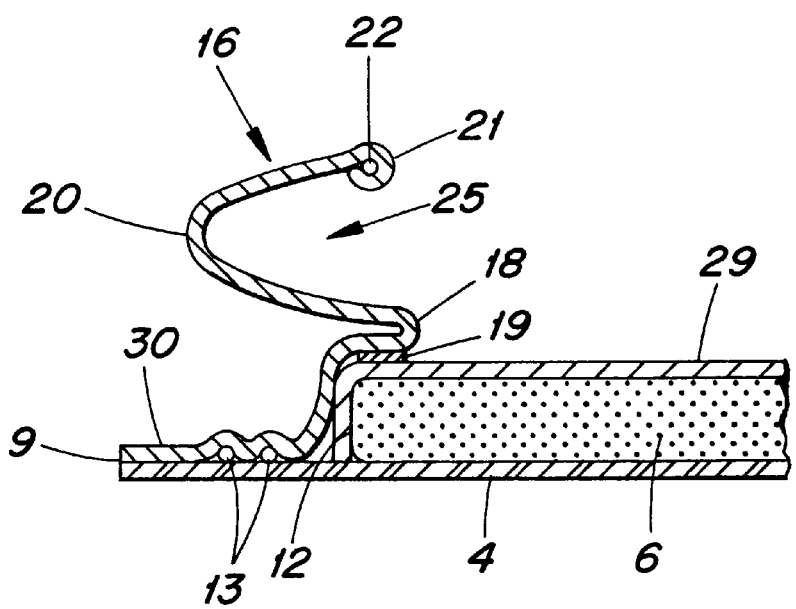

According to the embodiment of FIGS. 8 and 9, the inner sheet 5 which, in the preceding embodiments, extends over the whole width of the diaper and therefore covers the absorbent pad 6 in its entirety, is replaced by a tape 29 of a constant width which is slightly greater than the width that the pad 6 has in the crotch part 3. This tape 29, which extends over the whole length of the diaper and is arranged in a middle position between the opposed lengthwise edges 8 of the diaper, therefore covers the pad 6 over the whole width in the crotch part 3, as shown in FIG. 9, and only over the middle part of the width in the rear part 1 (and in the front part 2), as shown in FIG. 8.

Each of the two flaps 16 is here made in a single piece with a side tape 30 which, on each side of the diaper, covers the outer sheet 4 and the pad 6 on their parts which are not covered by the middle tape 29 and therefore replaces here the inner sheet 5 of the preceding embodiments. The tape 30 is fastened along the lengthwise line or strip 19 to the tape 29 along the side edge of the latter, and is extended laterally beyond this line 19 to form the flap 16. According to FIGS. 8 and 9, the tape 30 is then folded back outwards along a first fold line, defining the proximal edge 18 of the flap 16, and then folded back onto itself inwards along the fold line 20, the free edge of the tape 30 being folded back onto an elastic member 22 fastened to the tape 30 to form the elasticised distal edge 21 of the flap 16. Finally, as shown in FIG. 8, the flap 16 is fastened flat in the folded-back state in the rear part 1 (and in the front part 2) of the diaper by transverse lines or strips 23 and 24, whereas according to FIG. 9, it is free and can therefore be raised to form a pouch 25 in the crotch part 3, its distal edge 21 nevertheless remaining positioned substantially above its proximal edge 18.

In this embodiment too, of course, the flaps 16, instead of being folded back so as to form pouches 25 which are open inwards, could be folded back in the way illustrated by FIGS. 4 and 5.

In the embodiments according to FIGS. 1 to 3 and 4 and 5, the tapes 17 forming the flaps 16 can be made from sheets of liquid-permeable materials, for example hydrophobic nonwovens, or preferably liquid-impervious ones, for example nonwovens lined with an impervious film or coating.

In the embodiment according to FIGS. 6 and 7 the tape 26 must consist of a liquid-permeable material which may be hydrophobic or impervious to liquids in the region of the side parts 28 forming the flaps 16. By way of example, the tape 26 may consist of a hydrophobic nonwoven made hydrophilic only in the middle part 27. Thus, the two layers of nonwoven (tape 26 and inner sheet 5) covering the absorbent pad 6 in the region which receives the micturitions first, whilst promoting the entry of the fluids in the direction of the absorbent pad, limit the rise of fluids in the other direction. The side parts 28 forming the flaps 16, owing to their hydrophobic nature, then reduce the rewetting and hence improve the "keeping dry". In the example of FIGS. 8 and 9 the liquid-permeable middle tape 29 may consist, for example, of a nonwoven made hydrophilic, and the two side tapes 30 may consist, for example, of a hydrophobic nonwoven or a nonwoven made impervious to liquids, for example lined with an impervious film or coating on the face which is not in contact with the user's body, that is to say the face turned towards the outer support sheet 4.

Furthermore, it should be noted that in order to form a sheet which is hydrophilic in its middle part and hydrophobic in its two side parts, as is advantageously the case with the inner sheet 5 of the embodiments of FIGS. 1 to 3, 4 and 5 as well as 6 and 7 and in the case of the tape 26 of the embodiment of FIGS. 6 and 7, it is possible to employ a nonwoven which has a middle lengthwise strip or region exhibiting a structure that is different from that of the two side lengthwise strips or regions arranged on either side of this middle strip, this different structure being obtained by a change in the ratio of the two components (filaments and fibres) constituting the nonwoven. The hydrophilic and hydrophobic properties of these strips or regions of the nonwoven can also be obtained by surface treatments using strips or regions of the nonwoven.

It should additionally be noted that the fastening lines or strips 19, 23, 24, when providing fastening by adhesive bonding, may be produced either by application, at the time of the fastening, of adhesive in the form of hot-melt adhesive to the sheets or tapes to be fastened, or by reactivation, at the time of the fastening, of heat-reactivable hot-melt adhesive applied before the fastening to the sheets or tapes to be fastened.

Finally, while the elasticised distal edge 21 of the flaps 16 is defined in the description as being situated substantially above the proximal edge 18 of the flaps, it should be noted that, within the scope of the invention, the two folds of each of these flaps may have unequal widths capable of varying between approximately ⅓ and ⅔ of the total width of the flap between the proximal edge and the distal edge.

Although the invention has been described above and illustrated by the attached drawings in its application to a diaper of anatomical or hourglass shape comprising an hourglass-shaped absorbent pad, which may be intended for children or incontinent adults, it is obvious that it can also be applied to diapers which are not hourglass-shaped or which comprise absorbent pads of a shape other than that of an hourglass, as well as generally to any articles of hygiene which have the same general structure as diapers.

What is claimed is:

1. A disposable absorbent article of hygiene of generally rectangular shape with opposed lengthwise edges and opposed transverse edges, said article further comprising:

a liquid-impervious support sheet having an inner face, lengthwise edges and transverse edges, an absorbent pad having an inner surface and having lengthwise edges and transverse edges defining a pad periphery, the absorbent pad being arranged on and fastened to the inner face of the support sheet, the pad periphery defining a size smaller than a size of the support sheet so that the lengthwise and transverse edges of the absorbent pad are spaced inward toward a center region of the article relative to the lengthwise and transverse edges of the support sheet, a liquid-permeable cover sheet having an inner face and at least partially covering the inner face of the absorbent pad and fastened at least partially to the support sheet about the periphery of the absorbent pad, lengthwise elastic members fastened in a stretched state to the support sheet transversely outward of the lengthwise edges of the absorbent pad, two transversely spaced side flaps arranged on the inner face of the cover sheet, along the lengthwise edges of the article of hygiene, each of the flaps having a proximal portion fastened to the cover sheet and a distal edge having lengthwise elastic members fastened in a stretched state thereto, each of the flaps being fastened to the cover sheet by the proximal portion over a whole length of the article of hygiene and positioned with the fastened proximal portion transversely inward of the respective lengthwise edge of the absorbent pad over the whole length of the absorbent pad, and fastening means, disposed in a vicinity of one of the transverse edges of the article of hygiene, for closing the article of hygiene around a user's waist so that the article of hygiene defines a front end region adjacent one of the transverse edges and a rear region adjacent the other of the transverse edges and a crotch region corresponding to an intermediate region between the two end regions, wherein each flap is formed by a tape folded back onto itself over a whole length of the tape toward a lengthwise center of the article along a lengthwise fold line situated between the proximal portion and the distal edge and wherein lengthwise end portions of the folded tape are fastened flat to the cover sheet in the two end regions of the article of hygiene, so that the elasticized distal edge of the flap is located substantially adjacent the proximal portion over a whole length of the flap and a pouch formed by the folded tape opens toward the lengthwise center of the crotch region, the pouch being disposed substantially transversely outward of the absorbent pad in the crotch region only.

2. The disposable absorbent article of hygiene according to claim 1, wherein each of the two flaps is formed by an individual tape, the two tapes disposed with a transverse space therebetween.

3. The disposable absorbent article of hygiene according to claim 1, wherein the two flaps comprise portions of a single tape having two opposed, elasticized side edges forming the distal edges and which tape is fastened to the cover sheet at two lengthwise lines located transversely inwards of the side edges, the lengthwise lines forming the proximal portions, wherein two side parts of the tape between the side edges and the lengthwise fastening lines are folded to form the pouches, and wherein at least a middle part of the tape situated between the lengthwise fastening lines is permeable to liquids.

4. The disposable absorbent article of hygiene according to claim 3, wherein the tape comprises a liquid-permeable material which is hydrophilic in the middle part and hydrophobic or impervious to liquids in the side parts.

5. The disposable absorbent article of hygiene according to claim 1, wherein the cover sheet comprises a liquid-permeable middle tape having a width greater than a width of the pad in the crotch region and wherein each of the two side flaps comprises an individual side tape disposed adjacent a respective lengthwise edge of the article and which covers parts of the support sheet and parts of the pad which are not covered by the middle tape, wherein each of the side tapes is fastened to the middle tape at a lengthwise line located within the periphery of the pad and has a portion extending from the line, the extended portion forming one of said two spaced side flaps.

6. The disposable absorbent article of hygiene according to claim 5, wherein each side tape consists of a hydrophobic or liquid-impervious material.

7. The article of hygiene according to claim 1, wherein said pad periphery is hourglass-shaped.

* * * * *